US008900714B2

(12) United States Patent
Iwamori et al.

(10) Patent No.: US 8,900,714 B2
(45) Date of Patent: Dec. 2, 2014

(54) MEDICAL APPLIANCE HAVING POLYIMIDE FILM AND METHOD FOR MANUFACTURE THEREOF

(75) Inventors: Satoru Iwamori, Kanazawa (JP); Hiraku Murayama, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 2129 days.

(21) Appl. No.: 11/921,448

(22) PCT Filed: May 31, 2006

(86) PCT No.: PCT/JP2006/310867
§ 371 (c)(1),
(2), (4) Date: Dec. 3, 2007

(87) PCT Pub. No.: WO2006/129702
PCT Pub. Date: Dec. 7, 2006

(65) Prior Publication Data
US 2009/0234247 A1    Sep. 17, 2009

(30) Foreign Application Priority Data
Jun. 2, 2005   (JP) .................. 2005-162858

(51) Int. Cl.
C23C 14/12    (2006.01)
C23C 14/34    (2006.01)
A61M 25/09    (2006.01)
A61M 25/00    (2006.01)

(52) U.S. Cl.
CPC ................ A61M 25/09 (2013.01); C23C 14/34 (2013.01); A61M 2025/09083 (2013.01); C23C 14/12 (2013.01); A61M 25/0045 (2013.01)

USPC .......... 428/435; 428/34.7; 428/35.7; 428/327; 428/395; 428/423.5; 428/423.7; 600/434; 600/585

(58) Field of Classification Search
USPC ........ 600/434, 585; 428/34.7, 35.7, 327, 395, 428/423.5, 423.7, 435
See application file for complete search history.

(56) References Cited

U.S. PATENT DOCUMENTS

| 5,683,757 A * | 11/1997 | Iskanderova et al. ......... 427/525 |
| 8,414,506 B2 * | 4/2013 | Reynolds et al. ............ 600/585 |
| 2009/0234247 A1 * | 9/2009 | Iwamori et al. ............. 600/585 |

FOREIGN PATENT DOCUMENTS

| JP | 61-183459 A | 8/1986 |
| JP | 63-128167 A | 5/1988 |
| JP | 2-80241 A | 3/1990 |

(Continued)

OTHER PUBLICATIONS

Translation of JP 2001-346884, Apr. 16, 2001.*
International Search Report for PCT/JP2006-310867 dated Jul. 1, 2006.

(Continued)

*Primary Examiner* — Sean Dougherty
(74) *Attorney, Agent, or Firm* — Buchanan Ingersoll & Rooney PC

(57) ABSTRACT

Provided is a medical appliance excellent in slidability and durability. A medical appliance comprising a base material, a polyimide film (A) and a polymer film (B) having a higher nitrogen content and/or a higher oxygen content than respective contents of the polyimide film (A). The appliance has the polymer film (B) on a part or the whole of the surface of the base material, and has the polyimide film (A) on the polymer film (B).

16 Claims, 2 Drawing Sheets

(56) References Cited

FOREIGN PATENT DOCUMENTS

| | | |
|---|---|---|
| JP | 2001-238963 A | 9/2001 |
| JP | 2001-346884 A | 12/2001 |
| JP | 2003-135603 A | 5/2003 |
| JP | 2003-225311 A | 8/2003 |
| WO | WO 02/24245 A1 | 3/2002 |

OTHER PUBLICATIONS

English language translation of International Preliminary Report on Patentability.

English language translation of International Preliminary Report on Patentability, Jul. 1, 2006.

* cited by examiner

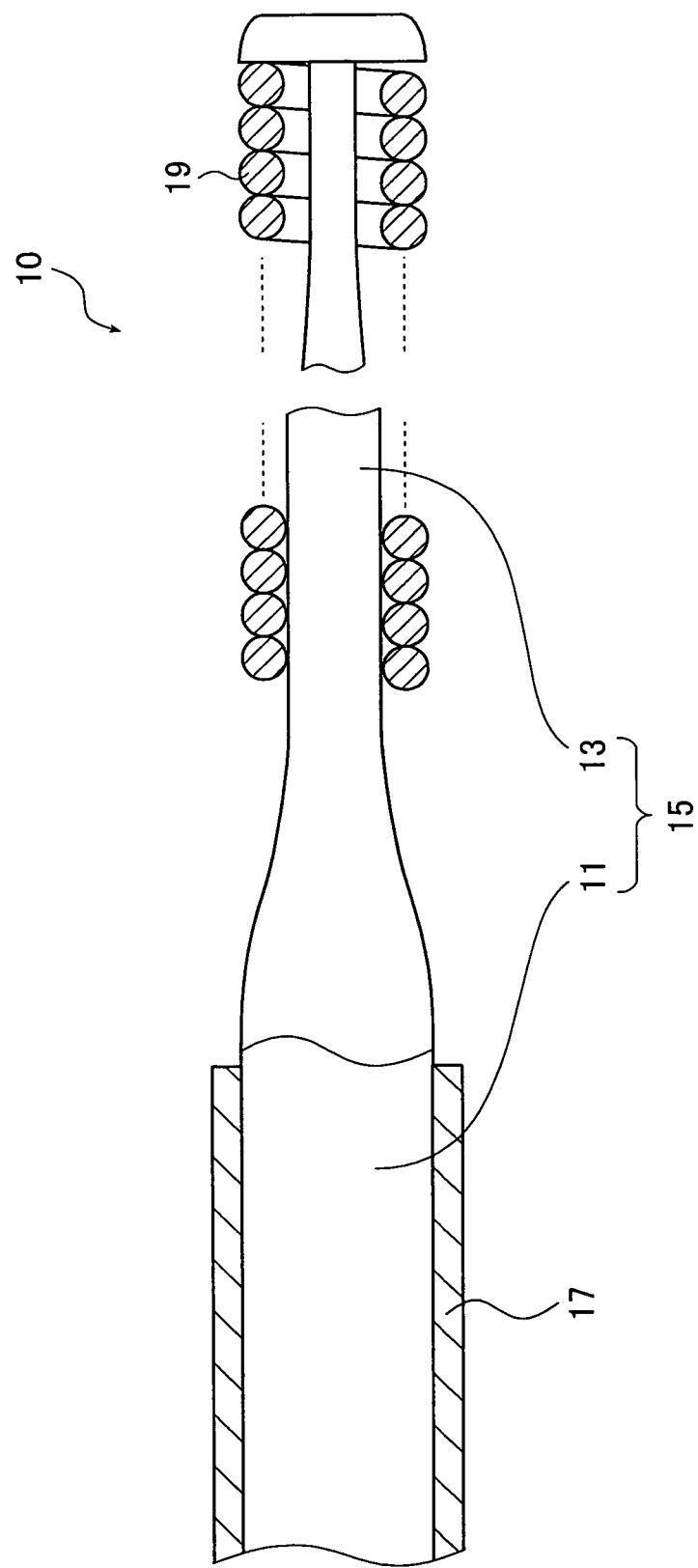

MEDICAL APPLIANCE HAVING POLYIMIDE FILM AND METHOD FOR MANUFACTURE THEREOF

TECHNICAL FIELD

The present invention relates to a medical appliance. More particularly, it relates to medical appliances such as a medical guide wire that are superior in slidability and durability.

BACKGROUND ART

Polyimides are polymers synthesized from bifunctional carboxylic anhydrides and primary diamines; among polyimides, aromatic ones exhibit superior mechanical characteristics, heat resistance and oxidation resistance, so they are extensively used in such fields as electronic devices and aircrafts.

In addition, polyimides also excel in lubricating property and biocompatibility, so using them as solid lubricating films and the like that are formed on substrates is under review in such fields as medical appliances.

A specific example that has been proposed is a medical wire insert characterized by having a coated wire comprising a core wire and a polyimide coat formed on its surface by vapor deposition polymerization (see Patent Document 1). According to Patent Document 1, the medical wire insert has high lubricating property, can smoothly travel through a medical annular device, has a suitable degree of stiffness, is easy to handle, and even has great peel strength.

Patent Document 1: JP 2001-238963 A

DISCLOSURE OF THE INVENTION

Problems to be Solved by the Invention

Now, medical appliances, in particular, guide wires that are used to introduce catheters require high adhesion between the substrate and the coat. This is because if the coat separates from the core of the guide wire during its handling, fragments of the separated coat might block the lumen of the guide wire or a peripheral blood vessel, potentially causing serious damage to the living body.

Nevertheless, the medical insert described in Patent Document 1 does not have sufficient adhesion between the above-described polyimide coat and the core wire so that the polyimide coat might come off under a great stress or during prolonged use.

Hence, a more durable and reliable medical appliance has been desired.

An object of the present invention is to provide a medical appliance excellent in slidability and durability.

Means for Solving the Problems

As a result of intensive studies, the present inventors found that by coating a surface of a substrate with a polymer film having high nitrogen atomic content and/or high oxygen atomic content, which in turn was overlaid with a polyimide film, there was obtained a medical appliance excellent in slidability and durability; the present invention has accordingly been accomplished.

Thus, the present invention provides the following (1)-(17).

(1) A medical appliance comprising a substrate, a polyimide film (A), and a polymer film (B) having a higher nitrogen atomic content and/or oxygen atomic content than the polyimide film (A), the substrate having the polymer film (B) in a partial or entire portion of a surface and also having the polyimide film (A) on top of the polymer film (B).

(2) The medical appliance according to (1) above, wherein the polymer film (B) comprises a polymer that is based on a polyimide and which has nitrogen atoms and/or oxygen atoms introduced into a molecular structure of the polyimide.

(3) The medical appliance according to (1) or (2) above, wherein a polyimide of which the polyimide film (A) is composed and/or the polyimide serving as a base of the polymer film (B) is at least one member selected from the group consisting of polyimides having structures represented by following formulas (I)-(III):

[Chemical Formula 1]

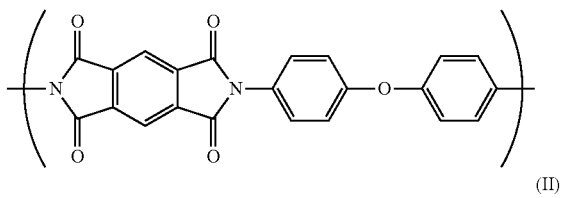

(I)

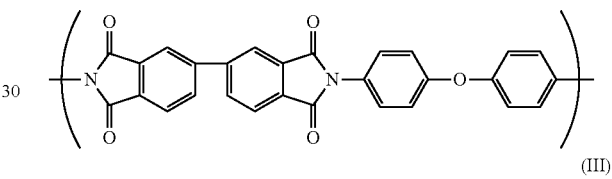

(II)

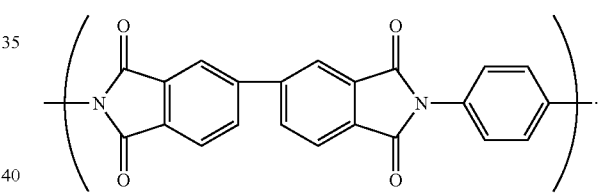

(III)

(4) The medical appliance according to any one of (1) to (3) above, wherein a polyimide of which the polyimide film (A) is composed is a fluorinated polyimide.

(5) The medical appliance according to any one of (1) to (4) above, wherein the polyimide film (A) and/or the polymer film (B) has been formed by reactive sputtering.

(6) The medical appliance according to (5) above, wherein the polymer film (B) has been formed by the reactive sputtering using a feed gas containing at least nitrogen.

(7) The medical appliance according to (6) above, wherein the feed gas further contains oxygen.

(8) The medical appliance according to any one of (5) to (7) above, wherein the polyimide film (A) has been formed by the reactive sputtering using a feed gas containing at least a fluorine-containing gas.

(9) The medical appliance according to any one of (1) to (8) above, wherein the substrate is made of a metal.

(10) The medical appliance according to any one of (1) to (8) above, wherein the substrate is a metallic wire.

(11) The medical appliance according to (10) above, wherein the metallic wire is a nickel-titanium alloy wire or a stainless steel wire.

(12). The medical appliance according to any one of (1) to (11) above, which is a guide wire comprising a wire including a wire body and a coil-fitting portion formed as an integral part of the wire body at its distal end, a coating layer formed on a surface of the wire body and a coil fitted around the coil-fitting portion.

(13) A method for manufacturing the medical appliance according to any one of (1) to (12) above, which comprises:
   a polymer film (B) production step of forming the polymer film (B) in the partial or entire portion of the surface of the substrate; and
   a polyimide film (A) production step of forming the polyimide film (A) on top of the polymer film (B) after the polymer film (B) production step.

(14) The method according to (13) above, wherein the polymer film (B) is formed in the partial or entire portion of the surface of the substrate by reactive sputtering during the polymer film (B) production step.

(15) The method according to (14) above, wherein the polymer film (B) is formed in the partial or entire portion of the surface of the substrate by the reactive sputtering using a feed gas containing at least nitrogen during the polymer film (B) production step.

(16) The method according to any one of (13) to (15) above, wherein the polyimide film (A) is formed on top of the polymer film (B) by reactive sputtering during the polyimide film (A) production step.

(17) The method according to (16) above, wherein the polyimide film (A) is formed on top of the polymer film (B) by the reactive sputtering using a feed gas containing at least a fluorine-containing gas during the polyimide film (A) production step.

Effects of the Invention

The medical appliance of the present invention excels in slidability and durability.

In addition, according to the method of the present invention for manufacture of a medical appliance, one can produce with comparative ease the medical appliance of the present invention which is excellent in slidability and durability.

BRIEF DESCRIPTION OF THE DRAWINGS

FIG. 3 shows in longitudinal section an example of the guide wire of the present invention.

LEGEND

Figure 1:
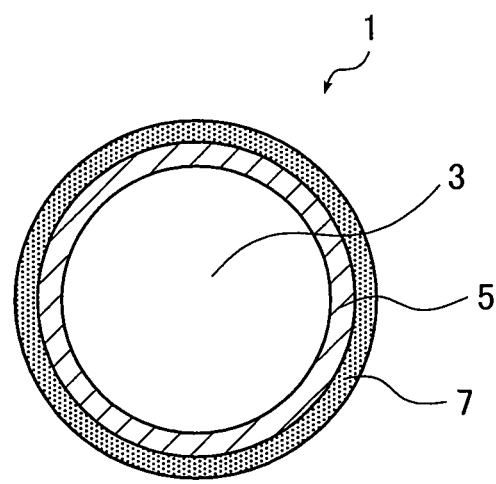
FIG. 1 shows in cross section an example of the medical appliance of the present invention.

1 Medical appliance of the present invention
3 Substrate
5 Polymer film (B)
7 Polyimide film (A)
10 Guide wire of the present invention
11 Wire body
13 Coil-fitting portion
15 Wire
17 Coating layer
19 Coil

BEST MODE FOR CARRYING OUT THE INVENTION

On the following pages, the medical appliance of the present invention is described in detail by reference to the preferred embodiment depicted in the drawings. It should, however, be noted that the present invention is by no means limited to this embodiment.

FIG. 1 shows in cross section an example of the medical appliance of the present invention.

The medical appliance of the present invention which is generally indicated at 1 comprises a substrate 3, a polyimide film (A) 7, and a polymer film (B) 5 having a higher nitrogen atomic content and/or oxygen atomic content than polyimide film (A) 7, substrate 3 having polymer film (B) 5 in a partial or the entire portion of the surface and also having polyimide film (A) 7 on top of polymer film (B) 5.

The material of the above-described substrate 3 is not limited in any particular way and various materials can be used. Specifically, they include, for example, metals such as nickel (Ni), titanium (Ti), stainless steel, copper, aluminum, iron, Ni—Ti containing alloys, and Co-base alloys such as cobalt (Co)—Ni-chromium containing alloys, as well as resins such as polyimides and polyamides.

The shape of substrate 3 is not limited in any particular way and substrates of various shapes can be used. Specifically, they include, for example, substrates in the form of a flat sheet, a rod or a string or substrates having three-dimensional shapes.

Particularly in the case where the medical appliance of the present invention is something like a guide wire, substrate 3 is preferably a metallic wire, more preferably a nickel-titanium alloy wire or a stainless steel wire.

The diameter of the wire is not limited in any particular way but it is preferably from about 0.1 to about 10 mm, more preferably from about 0.2 to about 1.0 mm.

Polymer film (B) 5 is formed in a partial or the entire portion of the surface of substrate 3 and polyimide film (A) 7 is formed on top of it.

Polymer film (B) 5 is not limited in any particular way so long as it is a polymer film having a higher nitrogen atomic content and/or oxygen atomic content than polyimide film (A) 7, and specific examples include polymer films that are based on polyimide, polyamide, polyamideimide, etc. and which have nitrogen atoms and/or oxygen atoms introduced into their molecular structures. Particularly preferred are polymer films that are based on polyimide and which have nitrogen atoms and/or oxygen atoms introduced into the molecular structure of the polyimide. This polyimide-based polymer film (B) 5 shows better adhesion to polyimide film (A) 7. Introduction of nitrogen atoms and/or oxygen atoms into the base polymer can be accomplished with comparative ease by the reactive sputtering process to be described later.

Alternatively, polymer film (B) can be formed using a bulk of polymer which has a higher nitrogen atomic content and/or oxygen atomic content than polyimide film (A) 7.

The polyimide serving as the base of the above-described polymer film (B) 5 is not limited in any particular way and can appropriately be selected from among known polyimides in consideration of the film deposition technique and the like. A specific, advantageous example is at least one member of the group consisting of a polyimide (pyromellitic dianhydride-oxydianiline) having the structure represented by the following formula (I), a polyimide (biphenyl dianhydride-oxydianiline) having the structure represented by the following formula (II), and a polyimide (biphenyl dianhydride-p-phenylene diamine) having the structure represented by the following formula (III). Using these polyimides, one can obtain a result that excels in heat resistance, mechanical characteristics, electrical characteristics, chemical resistance, UV resistance, radiation resistance, and the like.

Commercial products of these polyimides may be used. Examples for the polyimide having the structure represented by the following formula (I) include Kapton® (product of DU PONT-TORAY CO., LTD.) and APICAL® (product of Kaneka Corporation), and examples for the polyimide having the structure represented by the following formula (II) and the polyimide having the structure represented by the following formula (III) include Upilex® (product of UBE INDUSTRIES, LTD.) and the like.

[Chemical Formula 2]

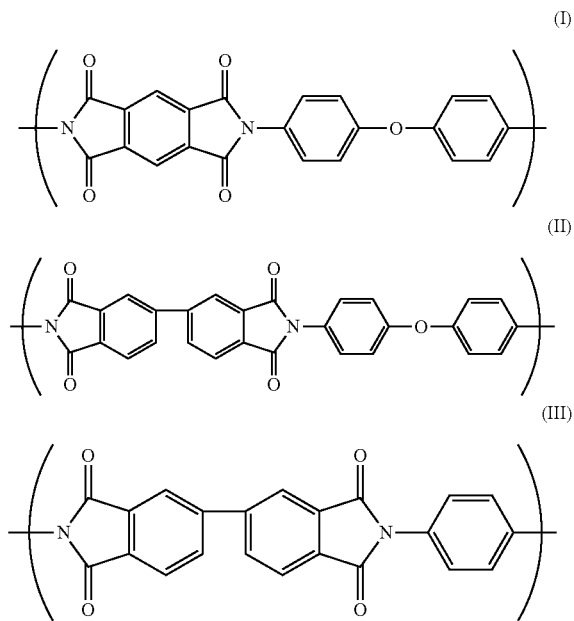

The thickness of polymer film (B) 5 is not limited in any particular way but in view of the comparative ease with which a uniform thickness can be obtained and the resulting economy, it is preferably 0.01-100 μm, more preferably 0.1-10 μm.

The method of forming polymer film (B) 5 is not limited in any particular way but, specifically, reactive sputtering may be mentioned as an advantageous example. According to this process, one can form a coat that is thin, uniform and has great peel strength.

It is particularly preferred to form polymer film (B) 5 by reactive sputtering using a feed gas containing at least nitrogen. According to this method, nitrogen atoms can be introduced into the molecular structure of the target material (say, polyimide) to facilitate the formation of polymer film (B) 5 having a higher nitrogen atomic content than polyimide film (A) 7.

If, for example, nitrogen alone or a gaseous mixture of nitrogen and argon is used, one can obtain polymer film (B) 5 having high nitrogen atomic content.

In another preferred embodiment, polymer film (B) 5 may be formed by reactive sputtering using a feed gas containing at least nitrogen and oxygen.

According to this method, nitrogen atoms and oxygen atoms can be introduced into the molecular structure of the target material to facilitate the formation of polymer film (B) 5 having a higher nitrogen atomic content and oxygen atomic content than polyimide film (A) 7.

In the case where the above-described feed gas is a gaseous mixture of nitrogen and oxygen (which may solely be composed of nitrogen), the volume ratio between nitrogen and oxygen ($N_2/O_2$) is preferably 100/0-100/20, more preferably 100/0-100/10. If the volume ratio between nitrogen and oxygen in the feed gas is within the stated range, the film deposition rate cannot be too slow to make efficient manufacture impossible.

The method of plasma generation is not limited in any particular way and DC, AC, RF or other methods may be employed. The apparatus to be used in reactive sputtering is not limited in any particular way and a conventional RF sputtering apparatus (e.g. SBH1104E; product of ULVAC, Inc.) or the like may be employed.

An example of the method of forming polymer film (B) on the substrate surface by the above-described reactive sputtering is described below. It should, however, be noted that the method of forming polymer film (B) is by no means limited to this example.

In the first step, the substrate is placed on one of the electrodes (anode electrode) in the vacuum chamber and the polyimide target is placed on the other electrode (cathode electrode). After evacuating it to a predetermined degree of vacuum, the vacuum chamber is supplied with the feed gas and RF is applied to produce plasma, whereby polymer film (B) is formed on the substrate surface.

The RF power required to generate plasma depends on the sizes of the vacuum chamber and the substrate but it generally ranges from about several watts to about one kilowatt. The treatment time also depends on the RF power and the amount of the substrate but it generally ranges from about several seconds to about several tens of minutes. Subsequently, evacuation is performed down to a predetermined pressure and, thereafter, a gas such as nitrogen is introduced into the vacuum chamber, from which the substrate is removed.

Usually, a polymer, say, polyimide in bulk form, that serves as the base of the above-described polymer film (B) 5 contains about several atomic percent of nitrogen atoms and from several to twenty atomic percent of oxygen atoms. Speaking of polyimide film (A) 7, if it is to be formed by RF sputtering with argon using the above-described bulk polyimide as the target, the nitrogen atomic content is smaller than that of the bulk material and the oxygen atomic content is also comparable to or smaller than that of the bulk material.

Speaking, on the other hand, of the above-described polymer film (B) 5, if it is to be formed by RF sputtering using nitrogen and oxygen as feed gases and also using the above-described bulk polyimide as the target, the contents of nitrogen atoms and oxygen atoms are higher than those of the bulk polyimide or the like, with the nitrogen atomic content usually being at least ten-odd atomic percent and the oxygen atomic content being at least 20 atomic percent.

Therefore, the above-described polymer film (B) 5, having comparatively large amounts of chemical bonds such as —C—O— and —C—N—, is believed to have higher affinity for substrate 3 (especially a metal substrate).

Note that the "atomic percent" refers to the ratio of the number of atoms of a particular species to the total number of atoms in the molecule.

The nitrogen atomic content of polymer film (B) 5, if it is based on polyimide, desirably has a higher nitrogen content than the bulk polyimide and this content, of course, varies with the structure of the polyimide; specifically, it is preferably from 1.2 to about 10 times, more preferably from about 2.0 to about 5.0 times, as large as in the bulk polyimide. Within this range, superior adhesion to the substrate is ensured.

Now speaking of the state of chemical bonds in polymers, this can be analyzed by X-ray photoelectron spectroscopy (XPS) and the like. Described below is the case where XPS analysis was performed using as bulk polyimide a polyimide (Upilex-S, product of UBE INDUSTRIES, LTD.) having the structure represented by the above formula (III) and also using AlKα as an X-ray source.

Figure 2:
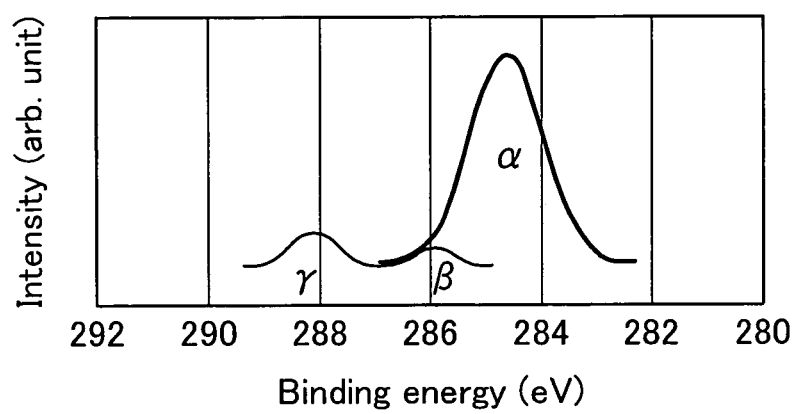
FIG. 2 shows an XPS C1s spectrum of a bulk polyimide (Upilex-S; product of UBE INDUSTRIES, LTD.).

FIG. 2 shows an XPS spectrum in the C (carbon) is region of the bulk polyimide (Upilex-S; product of UBE INDUSTRIES, LTD.)

As a result of the XPS analysis of the above-described bulk polyimide, three peaks were observed, peak α at about 284-285 eV, peak β at about 285.5-286.5 eV, and peak γ at about 287.5-288.5 eV. Peak α is assigned to a C—C bond, peak β to a C—N (nitrogen) bond or C—O (oxygen) bond, and peak γ to a C=O bond.

Considering the dependency on the type of bulk polyimide, if it is a polyimide having the structure represented by the above formula (III), the relative intensity $I_\beta$ of peak β to peak α is from about 0.04 to about 0.06, and the relative intensity $I_{\beta+\gamma}$ of peak β and peak γ to peak α is from about 0.14 to about 0.20.

In contrast, when polymer film (B) 5, which was formed by reactive sputtering using as the base a bulk polyimide having the structure represented by the above formula (III) and also using nitrogen as a feed gas, was subjected to XPS analysis by the same method as described above, relative intensities $I_\beta$ and $I_{\beta+\gamma}$ were both higher than the values for the bulk polyimide. For example, $I_\beta$ was from about 0.2 to about 20, preferably from about 0.5 to about 10, more preferably from about 1 to about 5, whereas $I_{\beta+\gamma}$ was from about 0.5 to about 50, preferably from about 1 to about 20, more preferably from about 2 to about 10.

Since polymer film (B) 5 has a higher nitrogen atomic content and/or oxygen atomic content than polyimide film, (A) 7, it has higher affinity for substrate 3 (especially a metal substrate), thus exhibiting superior adhesion. In addition, if polymer film (B) 5 is based on polyimide, it has superior adhesion to polyimide film (A) 7. Therefore, the medical material of the present invention excels in durability.

Polyimide film (A) 7 is formed on top of polymer film (B) 5. From the viewpoint of slidability, polyimide film (A) 7 is preferably formed in such a way as to cover the entire portion of the surface of polymer film (B) 5. In addition, as long as the effects of the present invention are not impaired, polyimide film (A) 7 may be formed on the surface of substrate 3 without providing polymer film (B) 5 as an intervening layer.

The polyimide that composes the polyimide film (A) is not limited in any particular way and a variety of polyimides may be used. Among these, a fluorinated polyimide is preferred since it excels in slidability. This fluorinated polyimide can, for example, be obtained by sputtering using a fluorinated aromatic diamine or a fluorinated aromatic dicarboxylic anhydride as a target, or by reactive sputtering using a fluorine-containing gas.

Examples of the above-mentioned fluorine-containing gas that may be used with advantage include not only fluorine but also fluorocarbons such as tetrafluoromethane, hexafluoroethane, hexafluoropentene, octafluoropropane, and octafluorocyclobutane.

An advantageous example of the polyimide that composes the polyimide film (A) is at least one member selected from the group consisting of a polyimide having the structure represented by the above formula (I), a polyimide having the structure represented by the above formula (II), and a polyimide having the structure represented by the above formula (III). Using these polyimides, one can obtain a result that excels in heat resistance, mechanical characteristics, electrical characteristics, chemical resistance, UV resistance, radiation resistance, and the like.

As long as the object of the present invention is not impaired, the polyimide film (A) may contain highly lubricating inorganic materials, fluororesins (e.g. polytetrafluoroethylene), and so forth.

The above-mentioned highly lubricating inorganic materials may specifically include, for example, molybdenum disulfide ($MoS_2$) and glass such as $SiO_2$.

The thickness of polyimide film (A) 7 is not limited in any particular way but in view of the comparative ease with which a uniform thickness can be obtained and the resulting economy, it is preferably 0.01-100 μm, more preferably 0.1-10 μm.

The method of forming polyimide film (A) 7 is not limited in any particular way but, specifically, reactive sputtering may be mentioned as an advantageous example. According to this process, one can form a coat that is thin, uniform and has great peel strength.

Feed gases that can be used in the above-mentioned reactive sputtering include argon, fluorine-containing gases such as tetrafluoromethane ($CF_4$), and mixtures of these gases. From the viewpoint of slidability of polyimide film (A) 7, the above-mentioned feed gases preferably contain nitrogen and oxygen in a total amount of not more than 1 vol % and, more preferably, they are free from nitrogen and oxygen.

Medical appliance 1 of the present invention which has polyimide film (A) 7 excels in low friction (slidability), wear resistance, corrosion resistance, and biocompatibility.

On the following pages, the method of the present invention for manufacture of a medical appliance is described.

The method of the present invention for manufacture of a medical appliance (which is hereinafter referred to as the "method for manufacture of the present invention") comprises the polymer film (B) production step of forming the above-described polymer film (B) in a partial or the entire portion of the surface of the above-described substrate, and the polyimide film (A) production step of forming the above-described polyimide film (A) on top of the above-described polymer film (B).

The method of forming the above-described polymer film (B) in a partial or the entire portion of the surface of the substrate in the above-described polymer film (B) production step is not limited in any particular way but examples include reactive sputtering, vapor deposition polymerization, and plasma-enhanced vapor deposition polymerization. Among these, reactive sputtering is preferred. This is because reactive sputtering can readily form a coat that is thin, uniform and has great peel strength.

If the polymer film (B) is to be formed by reactive sputtering, it is preferred to use a feed gas containing at least nitrogen. According to this method, nitrogen atoms can be introduced into the molecular structure of the target material (for example, polyimide) to facilitate the formation of the polymer film (B) having a higher nitrogen atomic content than the polyimide film (A).

If, for example, nitrogen alone or a gaseous mixture of nitrogen and argon is used, one can obtain the polymer film (B) having high nitrogen atomic content.

The above-described polymer film (B) production step can be performed in basically the same way as the method of producing the above-described polymer film (B). The above-described polyimide is preferably used as the target material. The feed gas that can be used is the same as the above-described feed gas. Prior to this step, a surface treatment step may be additionally provided for surface treatment such as cleaning or polishing the surface of the substrate.

The method of forming the above-described polyimide film (A) on top of the above-mentioned polymer film (B) in the above-described polyimide film (A) production step is not limited in any particular way but examples include reactive sputtering, vapor deposition polymerization, and plasma-enhanced vapor deposition polymerization. Among these, reactive sputtering is preferred. This is because reactive sputtering can readily form a coat that is thin, uniform and has great peel strength.

If the polyimide film (A) is to be formed by reactive sputtering, it is preferred to use a feed gas containing at least a fluorine-containing gas. According to this method, the target material (for example, polyimide) can be fluorinated to facilitate the formation of the polymer film (A) that excels in slidability.

Examples of the above-mentioned fluorine-containing gas that may be used with advantage include not only fluorine but also fluorocarbons such as tetrafluoromethane, hexafluoroethane, hexafluoropentene, octafluoropropane, and octafluorocyclobutane.

The above-described polyimide film (A) production step can be performed in basically the same way as the method of producing the above-described polyimide film (A). The above-described polyimide is preferably used as the target material. The feed gas that can be used is the same as the above-described feed gas.

Since the medical appliance of the present invention has the polyimide film (A), it is of low friction (slidable) and excels in wear resistance, corrosion resistance, and biocompatibility. In addition, having the polymer film (B) with excellent adhesion to both the substrate and the polyimide film (A), it also excels in durability. Further, if the polyimide film (A) and/or the polymer film (B) is formed by reactive sputtering, one can easily form a coat that is thin, uniform and has great peel strength.

In addition, according to the method of the present invention for manufacture of a medical appliance, the medical appliance of the present invention which excels in slidability and durability can be manufactured with comparative ease.

The medical appliance of the present invention can be used as a variety of medical appliances by taking advantage of its characteristics which, as described above, excel in slidability and durability. Specific examples are medical appliances for use in the living body, which include artificial organs, stents, catheters, guide wires, orthopedic materials (e.g. implants), medical patches, sutures, etc. A particularly advantageous use of the medical appliance of the present invention is as a guide wire.

On the following pages, the guide wire of the present invention is described in detail by reference to the advantageous embodiment depicted in the drawings. It should, however, be noted that the present invention is by no means limited to this embodiment.

FIG. 3 shows in longitudinal section an example of the guide wire of the present invention. As shown in FIG. 3, the guide wire of the present invention which is generally indicated by 10 comprises a wire 15 including a wire body 11 and a coil-fitting portion 13 formed as an integral part of wire body 11 at the distal end, as well as a coating layer 17 formed on the surface of wire body 11 and a coil 19 around coil-fitting portion 13.

In FIG. 3, its left side is referred to as the "proximal end" and the right side as the "distal end."

Guide wire 10 of the present invention may typically be used in treatments such as vascular dilation and stent implant against coronary artery stenosis, treatments against cerebral aneurysm and cerebral thrombosis, as well as drug infusion therapy as applied to the portal vein or hepatic artery in the case of liver cancer or the like. Depending on the mode of treatment, one may choose the site of wire 15 at which coating layer 17 is to be formed.

Coating layer 17 is composed of the polyimide film (A) and the polymer film (B) that are used in the above-described medical appliance of the present invention. Wire body 11 and coil 19 have the polymer film (B) on the surface of their specified areas and also have the polyimide film (A) on top of it.

As shown in FIG. 3, coating layer 17 can be formed in a partial or the entire portion of the surface of wire body 11. Coating layer 17 can be formed not only around wire body 11 but also on the surface of coil 19. In an embodiment where the guide wire of the present invention does not have coil 19, coating layer 17 may be formed in the entire portion of the surface of wire 15.

In one of its preferred embodiments, guide wire 10 of the present invention has a hydrophilic coat (not shown) in a partial or the entire portion of the surface of coil 19. The above-mentioned hydrophilic coat may be directly formed on the surface of coil 19 or it may be formed on top of coating layer 17 formed on the surface of coil 19. If desired, it may be formed on the surface of coil 19, with an intermediate layer capable of improved adhesion (say, the above-described polymer film (B)) being interposed.

The above-described hydrophilic coat is formed of a hydrophilic polymer. The hydrophilic polymer may be exemplified by polyethylene glycol derivatives, hyaluronic acid, polycarboxylic acid and derivatives thereof, as well as polyvinyl pyrrolidone and derivatives thereof, and so forth.

The above-described hydrophilic coat forms a strong water anchoring layer on its surface to exhibit high affinity for the blood within blood vessels and their inner surfaces, as well as display low friction (low friction coefficient).

The thickness of the above-described hydrophilic coat is not limited in any particular way but it is preferably from about 0.1 to about 5 µm, more preferably from about 1 to about 3 µm. If the thickness of the hydrophilic coat is within the stated range, adequate hydrophilicity can be imparted to guide wire 10 and, in addition, the diameter of guide wire 10 will in no case be unduly large.

The above-described hydrophilic coat can be formed by immersing the guide wire in a solution of a hydrophilic polymer, say, for example, polyvinyl pyrrolidine (PVP) in an organic solvent and then drying it.

Wire 15 is preferably tapered in an area near its distal end portion so that it can smoothly travel through a catheter. In this case, the tapered portion of wire 15 need not be tapered with a given angle but it suffices to be tapered toward the distal end portion.

Wire 15 may be so shaped as to have coil-fitting portion 13 in an area near its distal end, preferably in the above-described tapered portion, and coil 19 can be fitted around this coil-fitting portion 13. In other words, the site to be fitted with coil 19 is coil-fitting portion 13.

To fabricate wire 15, a wire (the first wire) including coil-fitting portion 13 and a wire (the second wire) including wire body 11 may be formed separately, then joined together to form a monolithic structure.

Alternatively, the distal end portion of a wire that can be used as wire 15 may be worked to form the tapered portion.

The cross-sectional shape of wire 15 is not limited in any particular way and may be exemplified by a circle, an ellipse, a square, a rectangle, etc., with a circle being preferred.

The length of wire 15 is not limited in any particular way but from the viewpoint of easy handling and the like, it is preferably from 0.3 to 3 m, more preferably from 0.8 to 2 m.

The diameter of wire 15 is not limited in any particular way but the diameter of wire body 11 is preferably from about 0.2 to about 2 mm whereas the diameter of the distal end of coil-fitting portion 13 is preferably from about 0.03 to about 0.5 mm. If the diameter of wire 15 is within the stated range, wire 15 can smoothly travel through a catheter and, in addition, it has a suitable degree of rigidity.

The material of the above-described wire 15 is not limited in any particular way but specific advantageous examples include radiolucent metals such as stainless steel and Ni—Ti containing alloys. In one preferred embodiment, the above-described first wire is composed of an alloy such as a Ni—Ti containing alloy that exhibits pseudoelasticity whereas the above-described second wire is composed of stainless steel or a cobalt-containing alloy.

Coil 19 is one obtained by shaping a wire in a spiral form and it is fitted around the above-described coil-fitting portion 13. Coil 19 imparts a suitable degree of suppleness and rigidity to the distal end portion of guide wire 10.

The cross-sectional shape of the wire that forms coil 19 is not limited in any particular way but in order to ensure that guide wire 10 can smoothly travel through a catheter and a blood vessel, it is preferably circular or elliptical, more preferably circular.

If the cross section of the wire that forms coil 19 is circular, the diameter of this wire is not limited in any particular way but because of such reasons as easy handling and high strength, it is preferably from about 10 to about 500 µm.

If the wire that forms coil 19 is a flat wire (with a rectangular cross section), its thickness is preferably from about 10 to about 500 µm and its width is preferably from about 20 to about 1500 µm.

The length of coil 19 is not limited in any particular way but the length along its longitudinal axis is preferably from 10 to 500 mm, more preferably from 30 to 300 mm.

The diameter of coil 19 is not limited in any particular way and is preferably from 0.15 to 3 mm, more preferably from 0.2 to 1 mm.

The pitch of coil 19 is not limited in any particular way and is preferably from 0 to 2 mm, more preferably from 0 to 0.05 mm.

The material of coil 19 is not limited in any particular way and may specifically be exemplified by, for example, stainless steel, superelastic alloys and cobalt-containing alloys, as well as noble metals such as gold, platinum and tungsten, or alloys containing the same. Particularly in the case where coil 19 is composed of radiopaque materials such as noble metals, guide wire 10 is opacified with respect to X-rays, providing a preferred result in that it can be inserted into the living body as the position of its distal end portion is being checked under radiographic guidance.

If desired, coil 19 may be composed of different materials in its distal and proximal end portions. For instance, the distal end portion may be composed of a radiopaque material in coil form whereas the proximal end portion is composed of a material in coil form that permits reasonable transmission of X-rays (as exemplified by stainless steel).

If desired, coil 19 may be replaced by a plastic jacket. In this case, the components are a wire 15 including wire body 11 and a plastic jacket coating portion formed integrally at the distal end of wire body 11, a coating layer 17 formed on the surface of wire body 11, and a plastic jacket applied around the plastic jacket coating portion. The material of the plastic jacket may be exemplified by polyurethane. A hydrophilic coat is provided on the surface of the plastic jacket. If desired, a layer equivalent to coating layer 17 may be provided on the surface of the plastic jacket.

The method for manufacturing guide wire 10 of the present invention is not limited in any particular way and any conventionally known method may be employed. In an exemplary case, coating layer 17 is formed by the above-described reactive sputtering in a predetermined area of the surface of wire 15. Subsequently, coil 19 having a hydrophilic coat preliminarily formed on the surface is fitted around coil-fitting portion 13 of this wire 15, whereby guide wire 10 of the present invention can be obtained.

Guide wire 10 of the present invention excels in lubricating property and can smoothly travel through a catheter or the living tissue. In addition, coating layer 17 shows good adhesion to wire body 11 and coil 19, so the chance of coating layer 17 to come off within the catheter or the living tissue is low enough to provide high reliability.

EXAMPLES

On the following pages, the present invention is explained specifically by reference to examples, to which the present invention is by no means limited.

Example 1

A 3-mm thick copper substrate (50 mm×50 mm) was provided, cleaned ultrasonically in acetone, and placed in an RF sputtering apparatus (SBH 1104E, product of ULVAC, Inc.). Subsequently, a polyimide film having the structure shown in the above formula (III) (Upilex-S, product of UBE INDUSTRIES, LTD.) was placed as a target in the sputtering apparatus, which was evacuated, supplied with nitrogen gas, and operated to perform sputtering with an RF power of 150 W for a processing time of 30 minutes, to thereby form a 0.5-µm thick polymer film (B-1) on the copper substrate.

In the next step, the sputtering apparatus was evacuated again and the copper substrate having the polymer film formed thereon was placed in the RF sputtering apparatus (SBH 1104E, product of ULVAC, Inc.). Subsequently, a polyimide film having the structure shown in the above formula (III) (Upilex-S, product of UBE INDUSTRIES, LTD.) was placed as a target in the sputtering apparatus, which was supplied with argon gas and operated to perform sputtering with an RF power of 150 W for a processing time of 100 minutes to form a 0.5-µm thick polyimide film (A-1) on the above-described polymer film (B-1), thereby preparing a sample.

The elemental compositions (atom %) of the polymer film (B-1), polyimide film (A-1) and the bulk polyimide (Upilex-S, product of UBE INDUSTRIES, LTD.) in Example 1 are shown in the following Table 1.

[Table 1]

TABLE 1

|  | Carbon atom | Oxygen atom | Nitrogen atom |
| --- | --- | --- | --- |
| Bulk polyimide | 79 | 14 | 7 |
| Polyimide film (A-1) | 84 | 12 | 4 |
| Polymer film (B-1) | 21 | 21 | 58 |

(atom %)

As is clear from Table 1, the polyimide film (A-1) formed by using argon gas as the feed gas had slightly lower oxygen and nitrogen atomic contents than the bulk polyimide.

In comparison, the polymer film (B-1) formed by using nitrogen gas as the feed gas had higher oxygen and nitrogen atomic contents than the bulk polyimide and the polyimide film (A-1). Here the polymer film (B-1), despite the use of the nitrogen gas, had a higher oxygen atomic content and this would have resulted from the presence of residual oxygen in the apparatus that eventually got into the polyimide.

In addition, the polymer film (B-1) and the polyimide film (A-1) of Example 1 were analyzed for their composition and chemical state by X-ray photoelectron spectroscopy (XPS) (apparatus name: Quantum-2000, product of ULVAC-PHI, Inc.) and the C1s spectra were subjected to waveform separation to determine $I_\beta$ and $I_{\beta+\gamma}$.

The results are shown in Table 2.
[Table 2]

TABLE 2

|  | $I_\beta$ | $I_{\beta+\gamma}$ |
|---|---|---|
| Polyimide film (A-1) | 0.15 | 0.2 |
| Polymer film (B-1) | 2.4 | 3.2 |

Example 2

Except for replacing the copper substrate by a stainless steel (SUS 302) wire 100 mm long and 0.35 mm in diameter, the same procedure as in Example 1 was repeated to form a 0.5-μm thick polymer film (B-2) and a 0.5-μm thick polyimide film (A-2), thereby preparing a sample.

Example 3

Except for replacing the copper substrate by a Ni—Ti alloy wire 100 mm long and 0.35 mm in diameter, the same procedure as in Example 1 was repeated to form a 0.5-μm thick polymer film (B-3) and a 0.5-μm thick polyimide film (A-3), thereby preparing a sample.

Example 4

As in Example 1, a 3-mm thick copper substrate (50 mm×50 mm) was provided, cleaned ultrasonically with acetone, and placed in an RF sputtering apparatus (SBH 1104E, product of ULVAC, Inc.). Subsequently, a polyimide film having the structure shown in the above formula (III) (Upilex-S, product of UBE INDUSTRIES, LTD.) was placed as a target in the sputtering apparatus, which was evacuated, supplied with nitrogen gas, and operated to perform sputtering with an RF power of 150 W for a processing time of 30 minutes, to thereby form a 0.5-μm thick polymer film (B-1) on the copper substrate.

In the next step, the sputtering apparatus was evacuated again and the copper substrate having the polymer film formed thereon was placed in the RF sputtering apparatus (SBH 1104E, product of ULVAC, Inc.). Subsequently, a polyimide film having the structure shown in the above formula (III) (Upilex-S, product of UBE INDUSTRIES, LTD.) was placed as a target in the sputtering apparatus, which was supplied with a gas mixture of argon (Ar) and tetrafluoroethylene ($CF_4$) (mixing ratio; Ar:$CF_4$=10:1) and operated to perform sputtering with an RF power of 150 W for a processing time of 120 minutes, to thereby form a 0.5-μm thick polyimide film (A-4) on the above-described polymer film (B-1), thereby preparing a sample.

Comparative Example 1

The same procedure as in Example 1 was repeated to form a polymer film (B-1) on the copper substrate, thereby preparing a sample. The only difference about the sample of Comparative Example 1 was that the thickness of the polymer film (B-1) was set at 1.0 μm.

Comparative Example 2

A 3-mm thick copper substrate (50 mm×50 mm) was provided, cleaned ultrasonically with acetone, and placed in an RF sputtering apparatus (SBH 1104E, product of ULVAC, Inc.). Subsequently, a polyimide film having the structure shown in the above formula (III) (Upilex-S, product of UBE INDUSTRIES, LTD.) was placed as a target in the sputtering apparatus, which was evacuated, supplied with argon gas, and operated to perform sputtering with an RF power of 150 W for a processing time of 200 minutes, to thereby form a 0.5-μm thick polyimide film (A-5) on the above-mentioned copper substrate, thereby preparing a sample.

Comparative Example 3

Except for replacing the copper substrate by a stainless steel (SUS 302) wire 100 mm long and 0.35 mm in diameter, the same procedure as in Comparative Example 2 was repeated to form a 1.0-μm thick polyimide film (A-6), thereby preparing a sample.

Comparative Example 4

Except for replacing the copper substrate by a Ni—Ti alloy wire 100 mm long and 0.35 mm in diameter, the same procedure as in Comparative Example 2 was repeated to form a 1.0-μm thick polyimide film (A-7), thereby preparing a sample.

Using the respective samples obtained in Examples 1 and 4 as well as in Comparative Examples 1 and 2, evaluation of slidability and adhesion was performed by the methods described below. In addition, using the respective samples obtained in Examples 2 and 3 as well as in Comparative Examples 3 and 4, evaluation of peelability was performed by the method also described below.

The results are shown in Tables 3 and 4.
(Slidability)

Using a pin-on-disk friction tester (the evaluation equipment described in "Materials Science and Technology", Journal of the Materials Science Society of Japan, vol. 41, p. 326 (2004)), the friction coefficient was determined with the disk rotating at 5 rpm with a radius of 4 mm under a load condition of 20 g.

The results are shown in Table 3.
(Adhesion)

The adhesion between the substrate and thin film was determined by the method described in Technology Research Report, The Institute of Electronics, Information and Communication Engineers, OME 2004-96, p. 25 (2004). To be more specific, after treating the surface of each sample with an oxygen plasma under the conditions of 100 W and 10 seconds, the sample surface was bonded to a stud by means of a cyanoacrylate-based adhesive (trade name: ARON ALPHA, product of TOAGOSEI CO., LTD.), the movable stage was moved at a speed of 0.01 mm/s, and the force being applied at the moment peel occurred was measured to determine the adhesion.

When the peel occurred between the copper substrate and the polyimide film (A), the rating "poor" was given, and when the peel occurred between the polyimide film (A) and the stud, the rating "good" was given.

The results are shown in Table 3.

(Peelability)

Each sample was bent through 90 degrees five times and the resulting state was examined under an electron microscope (SEM) to check for any peel.

When the peel occurred between the substrate and the polyimide film (A), the rating "poor" was given, and when no peel occurred, the rating "good" was given.

The results are shown in Table 4.

[Table 3]

TABLE 3

|  | Ex. 1 | Ex. 4 | Comp. Ex. 1 | Comp. Ex. 2 |
|---|---|---|---|---|
| Slidability | 0.16 | 0.07 | 0.4 | 0.16 |
| Adhesion | Good | Good | Good | Poor |

[Table 4]

TABLE 4

|  | Ex. 2 | Ex. 3 | Comp. Ex. 3 | Comp. Ex. 4 |
|---|---|---|---|---|
| Peelability | Good | Good | Poor | Poor |

As is clear from the results shown in Table 3, the sample (Comparative Example 1) having only the polymer film (B-1) on the copper substrate excelled in adhesion but was low in slidability. The sample (Comparative Example 2) having only the polyimide film (A-5) on the copper substrate excelled in slidability but was low in adhesion. On the other hand, the sample having the polymer film (B-1) on the copper substrate and also having the polyimide film (A-1) or (A-4) on top of it (Examples 1 and 4) excelled in both slidability and adhesion.

In addition, as is clear from the results shown in Table 4, peel occurred in Comparative Examples 3 and 4 but not in Examples 2 and 3, thus attesting to their high durability.

The invention claimed is:

1. A medical appliance comprising a substrate, a polyimide film (A), and a polymer film (B) having a higher nitrogen atomic content and/or oxygen atomic content than the polyimide film (A), the substrate having the polymer film (B) on a partial or entire portion of a surface thereof, and the polyimide film (A) being on top of the polymer film (B), wherein the polymer film (B) comprises a polyimide polymer which has nitrogen atoms and/or oxygen atoms introduced into a molecular structure of the polyimide polymer, wherein a polyimide of which the polyimide film (A) is composed and/or the polyimide polymer of the polymer film (B) is at least one member selected from the group consisting of polyimides having structures represented by following formulas (I)-(III):

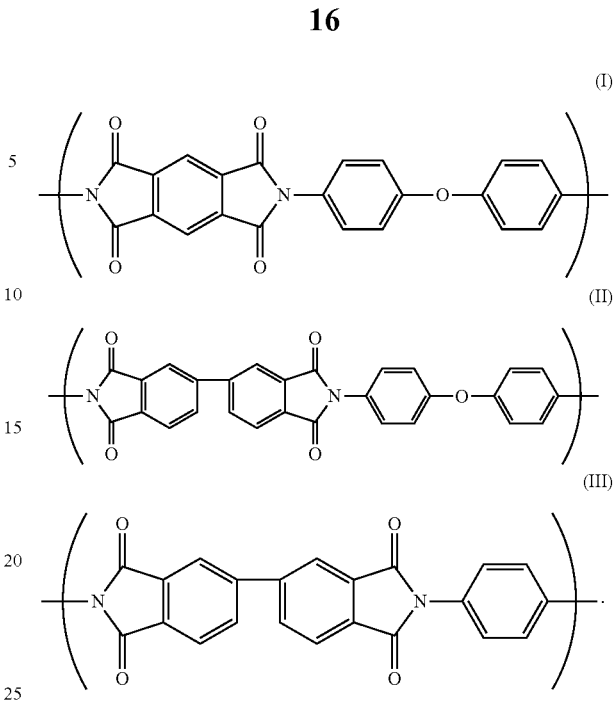

2. The medical appliance according to claim 1, wherein the polyimide of which the polyimide film (A) is composed is a fluorinated polyimide.

3. The medical appliance according to claim 1, wherein the polyimide film (A) and/or the polymer film (B) has been formed by reactive sputtering.

4. The medical appliance according to claim 3, wherein the polyimide film (A) has been formed by the reactive sputtering whose target material is a polyimide and which uses a feed gas containing at least a fluorine-containing gas.

5. The medical appliance according to claim 3, wherein the polymer film (B) has been formed by the reactive sputtering using as a base a polyimide having a structure represented by the formula (III) and also using a feed gas only composed of nitrogen.

6. The medical appliance according to claim 5, wherein, when analyzed by X-ray photoelectron spectroscopy using AlKα as an X-ray source, the polymer film (B) which has been formed by the reactive sputtering using as the base the polyimide having the structure represented by the formula (III) and also using the feed gas only composed of nitrogen has a relative intensity $I_\beta$ of peak β assigned to a C—N bond or a C—O bond to peak α assigned to a C—C bond of from 1 to 5.

7. The medical appliance according to claim 5, wherein, when analyzed by X-ray photoelectron spectroscopy using AlKα as an X-ray source, the polymer film (B) which has been formed by the reactive sputtering using as the base the polyimide having the structure represented by the formula (III) and also using the feed gas only composed of nitrogen has a relative intensity $I_{\beta+\gamma}$ of peak β assigned to a C—N bond or a C—O bond and peak γ assigned to a C=O bond to peak α assigned to a C—C bond of from 2 to 10.

8. The medical appliance according to claim 1, wherein the substrate is made of a metal.

9. The medical appliance according to claim 1, wherein the substrate is a metallic wire.

10. The medical appliance according to claim 9, wherein the metallic wire is a nickel-titanium alloy wire or a stainless steel wire.

11. The medical appliance according to claim 1, which is a guide wire comprising a wire including a wire body and a coil-fitting portion formed as an integral part of the wire body at a distal end of the wire body, a coating layer formed on a surface of the wire body and a coil fitted around the coil-fitting portion.

12. A method for manufacturing a medical appliance comprising a substrate, a polyimide film (A), and a polymer film (B) having a higher nitrogen atomic content and/or oxygen atomic content than the polyimide film (A), the substrate having the polymer film (B) on a partial or entire portion of a surface thereof, and the polyimide film (A) being on top of the polymer film (B), wherein the polymer film (B) comprises a polyimide polymer which has nitrogen atoms and/or oxygen atoms introduced into a molecular structure of the polyimide polymer, the method comprising:

a polymer film (B) production step of forming the polymer film (B) in the partial or entire portion of the surface of the substrate, wherein nitrogen atoms and/or oxygen atoms are introduced into a molecular structure of the polyimide by reactive sputtering; and a polyimide film (A) production step of forming the polyimide film (A) on top of the polymer film (B) after the polymer film (B) production step.

13. The method according to claim 12, wherein the polymer film (B) is formed in the partial or entire portion of the surface of the substrate by reactive sputtering during the polymer film (B) production step.

14. The method according to claim 13, wherein the polymer film (B) is formed in the partial or entire portion of the surface of the substrate by the reactive sputtering using a feed gas only composed of nitrogen during the polymer film (B) production step.

15. The method according to claim 12, wherein the polyimide film (A) is formed on top of the polymer film (B) by reactive sputtering during the polyimide film (A) production step.

16. The method according to claim 15, wherein the polyimide film (A) is formed on top of the polymer film (B) by the reactive sputtering whose target material is a polyimide and which uses a feed gas containing at least a fluorine-containing gas during the polyimide film (A) production step.

* * * * *